US009095691B2

(12) United States Patent
Schumacher et al.

(10) Patent No.: US 9,095,691 B2
(45) Date of Patent: *Aug. 4, 2015

(54) UV STABLE TRANSDERMAL THERAPEUTIC PLASTER WITH A UV ABSORBING SELF-ADHESIVE LAYER SEPARATED FROM THE DRUG MATRIX

(71) Applicant: Bayer Intellectual Property GmbH, Berlin (DE)

(72) Inventors: Jochen Schumacher, Bucha (DE); Manfred Suesse, Langenorla (DE); Michael Dittgen, Apola (DE); Stephan Mletzko, Berlin (DE); Jan-Peter Ingwersen, Berlin (DE); Thomas Langguth, Jena (DE); Dirk Schenk, Dietramszell (DE); Hubert Kaffl, Fischbachau (DE)

(73) Assignee: Bayer Intellectual Property GmbH, Berlin (DE)

( * ) Notice: Subject to any disclaimer, the term of this patent is extended or adjusted under 35 U.S.C. 154(b) by 117 days.

This patent is subject to a terminal disclaimer.

(21) Appl. No.: 13/835,723

(22) Filed: Mar. 15, 2013

(65) Prior Publication Data

US 2013/0226113 A1 Aug. 29, 2013

Related U.S. Application Data

(63) Continuation of application No. 10/545,826, filed as application No. PCT/EP2004/001052 on Feb. 4, 2004, now Pat. No. 8,486,443.

(30) Foreign Application Priority Data

Feb. 21, 2003 (EP) .................................. 03 003 888
Feb. 25, 2003 (EP) .................................. 03 004 061

(51) Int. Cl.

| | |
|---|---|
| *A61K 9/70* | (2006.01) |
| *A61M 35/00* | (2006.01) |
| *A61K 9/00* | (2006.01) |
| A61K 47/08 | (2006.01) |
| A61K 47/12 | (2006.01) |
| A61K 47/22 | (2006.01) |

(52) U.S. Cl.
CPC .............. *A61M 35/00* (2013.01); *A61K 9/0014* (2013.01); *A61K 9/7084* (2013.01); *A61K 47/08* (2013.01); *A61K 47/12* (2013.01); *A61K 47/22* (2013.01)

(58) Field of Classification Search
None
See application file for complete search history.

(56) References Cited

U.S. PATENT DOCUMENTS

| | | |
|---|---|---|
| 5,023,084 A | 6/1991 | Chien et al. |
| 5,106,891 A | 4/1992 | Valet |
| 5,128,124 A | 7/1992 | Fankhauser et al. |
| 5,128,284 A | 7/1992 | Olson et al. |
| 5,248,676 A | 9/1993 | Nakagawa et al. |
| 5,352,457 A | 10/1994 | Jenkins et al. |
| 5,376,377 A | 12/1994 | Gale et al. |
| 5,512,292 A | 4/1996 | Gale et al. |
| 5,538,736 A | 7/1996 | Hoffmann et al. |
| 5,560,922 A | 10/1996 | Chien et al. |
| 5,762,956 A | 6/1998 | Chien et al. |
| 5,788,984 A | 8/1998 | Guenther et al. |
| 5,858,394 A | 1/1999 | Lipp et al. |
| 5,866,157 A | 2/1999 | Higo et al. |
| 5,876,746 A | 3/1999 | Jona et al. |
| 5,904,931 A | 5/1999 | Lipp et al. |
| 5,906,830 A | 5/1999 | Farinas et al. |
| 5,948,433 A | 9/1999 | Burton et al. |
| 6,071,531 A | 6/2000 | Jona et al. |
| 6,143,319 A | 11/2000 | Meconi et al. |
| 6,238,284 B1 | 5/2001 | Dittgen et al. |
| 6,521,250 B2 | 2/2003 | Meconi et al. |
| 6,902,741 B1 | 6/2005 | Grawe et al. |
| 6,924,410 B2 | 8/2005 | Tsuruda et al. |
| 7,470,452 B1 | 12/2008 | Flosbach et al. |

(Continued)

FOREIGN PATENT DOCUMENTS

| | | |
|---|---|---|
| CA | 2 372 710 | 8/2000 |
| CA | 2 366 859 | 9/2001 |

(Continued)

OTHER PUBLICATIONS

Bjarnason et al., "Low doses of estradiol in combination with gestodene to prevent postmenopausal bone loss," American Journal of Obstetrics and gynecology, Sep. 2000, vol. 183, No. 3, pp. 550-560.

(Continued)

*Primary Examiner* — Kevin S Orwig
(74) *Attorney, Agent, or Firm* — Millen, White, Zelano & Branigan, P.C.

(57) ABSTRACT

The invention relates to a UV stable transdermal therapeutic system (TTS) consisting of a back layer, at least one matrix containing an active substance and optionally, a withdrawal film and an UV-radiation absorber. An adhesive layer containing said UV-radiation absorber is arranged between the back layer and the matrix containing an active substance which is distant as much as possible from a surface, a separation layer is arranged between the adhesive layer containing said UV-radiation absorber and the matrix containing an active substance, which is as remote as possible from the surface which is impermeable to the active substance and UV-radiation absorber. The inventive transdermal therapeutic system exhibits a high stability and is devoid of inconveniences of existing TTS containing a light-sensitive substance.

23 Claims, No Drawings

(56) References Cited

U.S. PATENT DOCUMENTS

| | | |
|---|---|---|
| 7,687,554 B2 | 3/2010 | Schellenberg et al. |
| 8,173,592 B1 | 5/2012 | Engel et al. |
| 2002/0004065 A1 | 1/2002 | Kanios et al. |
| 2003/0149385 A1 | 8/2003 | Tsuruda et al. |
| 2003/0152616 A1 | 8/2003 | Hartwig et al. |
| 2004/0009200 A1 | 1/2004 | Seyler et al. |
| 2004/0022836 A1 | 2/2004 | Degen et al. |
| 2005/0055975 A1 | 3/2005 | Tackett et al. |
| 2005/0129756 A1 | 6/2005 | Podhaisky et al. |
| 2005/0142175 A1 | 6/2005 | Langguth et al. |
| 2005/0175678 A1 | 8/2005 | Breitenbach et al. |
| 2006/0246122 A1 | 11/2006 | Langguth et al. |
| 2006/0251707 A1 | 11/2006 | Schumacher et al. |
| 2008/0063698 A1 | 3/2008 | Hartwig et al. |

FOREIGN PATENT DOCUMENTS

| | | |
|---|---|---|
| CA | 2 605 112 | 11/2006 |
| DE | 43 36 299 A1 | 5/1995 |
| DE | 44 03 487 | 8/1995 |
| DE | 199 06 152 | 8/2000 |
| DE | 199 12 623 A | 9/2000 |
| DE | 100 53 375 | 1/2002 |
| DE | 100 53 375 C1 | 1/2002 |
| EP | 0 285 563 | 10/1988 |
| EP | 0 483 370 | 3/1995 |
| EP | 0 787 488 | 8/1997 |
| EP | 976 405 | 2/2000 |
| EP | 1 121 941 | 8/2001 |
| EP | 1 197 212 | 4/2002 |
| EP | 1 269 999 | 1/2003 |
| EP | 1 452 173 | 9/2004 |
| EP | 1 541 137 | 6/2005 |
| JP | 59039827 | 3/1984 |
| JP | 60 069014 | 4/1985 |
| JP | 60166611 | 8/1985 |
| JP | 10 26537 A1 | 1/1989 |
| JP | 6 93217 | 4/1994 |
| JP | 09 315957 | 12/1997 |
| JP | 10-265371 | 10/1998 |
| JP | 2002 541122 | 12/2000 |
| WO | WO 90/04397 | 5/1990 |
| WO | WO 90 06736 | 6/1990 |
| WO | WO 92/07590 | 5/1992 |
| WO | WO 96 40355 | 12/1996 |
| WO | WO 97 38354 | 10/1997 |
| WO | WO 97/39743 | 10/1997 |
| WO | WO 99 66908 | 12/1999 |
| WO | WO 00/45797 | 8/2000 |
| WO | WO 00/56289 | 9/2000 |
| WO | WO 00 59542 | 10/2000 |
| WO | WO 01/37770 | 5/2001 |
| WO | WO 01/68061 | 9/2001 |
| WO | WO 02/34200 | 5/2002 |
| WO | WO 02/45701 | 6/2002 |
| WO | WO 03 077925 | 9/2003 |
| WO | WO 2004 058247 | 7/2004 |
| WO | WO 2004 073696 | 9/2004 |
| WO | WO 2005 023878 | 3/2005 |
| WO | WO 2005 058287 | 6/2005 |
| WO | WO 2006 117139 | 11/2006 |
| WO | WO 2010 042152 | 4/2010 |

OTHER PUBLICATIONS

Chatelain, Eric et al., "Photostabilization of Butyl Methozydibenzoylmethane . . . " Photochemistry and Photobiology, 2001, vol. 74, No. 3, pp. 401-406 (English).

Ciba Specialty Chemicals Tinosorb S brochure (2002).

European Search Report dated May 12, 2004.

Partial European Search Report dated Sep. 27, 2005.

Sitruk-Ware, R., "Transdermal Application of Steroids Hormones for Contraception," J. Steroid Biochem. Molec. Biol., 1995, vol. 53, No. 1-6, pp. 247-251.

Thomson Innovation, English Translation of Claims and Description, Retrieved from Thomson Innovation Record View on Jun. 14, 2010; English Abstract of WO1990004397.

Thomson Innovation, English Translation of Claims and Description, Retrieved from Thomson Innovation Record View on Jun. 14, 2010; English Abstract of EP1452173.

Thomson Innocation, English Translation of Claims and Description, Retrieved from Thomas Innovation Record View on Jul. 26, 2010; English Abstract of DE4336299.

Thomson Innocation, English Translation of Claims and Description, Retrieved from Thomas Innovation Record View on Jul. 26, 2010; English Abstract of DE 4403487.

Thomson Innocation, English Translation of Claims and Description, Retrieved from Thomas Innovation Record View on Jul. 26, 2010; English Abstract of DE19912623.

Sanken Kako KK, "Production of dibenxyls," Patent Abstracts of Japan, Publication Date: Jan. 27, 1989, English Abstract of JP-10-256371.

Hisamitsu Pharmaceut Co Inc., "Device for percutaneous therapy," Patent Abstracts of Japan, Publication Date: Dec. 9, 1997; English Abstract of JP-09 315957.

Sekisui Chem Co Ltd., "Transcutaneous Absorption Plaster," Patent Abstract of Japan, Publication Date: Oct. 6, 1998; Full English Translation of JP-10 265371.

Translation of Abstract of JP-59039827, Publication Date: Mar. 5, 1984.

Translation of Abstract of JP-60 069014, Publication Date: Apr. 19, 1985.

Translation of Abstract of JP-60166611, Publication Date: Aug. 29, 1985.

Brisaert M. and J.A. Plaizie-Vercammen.: "Investigation on the Photostability of a Tretinoin Lotion and Stabilzation With Additives." Proc 2nd World Meeting on Pharmaceutical Technology, APGI/APV, Paris, May 25-28, 1998, pp. 1231-1232 (English).

Translation of Abstract of JP-50030118, Publication Date: Mar. 10, 2004.

UV STABLE TRANSDERMAL THERAPEUTIC PLASTER WITH A UV ABSORBING SELF-ADHESIVE LAYER SEPARATED FROM THE DRUG MATRIX

This application is a continuation of U.S. Ser. No. 10/545,826, filed Aug. 17, 2005. U.S. Ser. No. 10/545,826 is a 371 US National stage application of PCT/EP04/01052, filed Feb. 4, 2004.

The invention relates to a novel UV-stable transdermal therapeutic system (TTS) which consists of a backing layer, of at least one active ingredient-containing matrix and optionally of a detachable sheet, and comprises a UV absorber, with at least one UV absorber-containing adhesive layer being provided between the backing layer and the active ingredient-containing matrix which is furthest away from the surface of the skin, and at least one separating layer which is impermeable to active ingredient and impermeable to the UV absorber being present between the adhesive layer containing the UV absorber and the active ingredient-containing matrix which is furthest away from the surface of the skin.

Attempts are known to employ photosensitive active ingredients which absorb UV-A and UV-B rays and normally in suncreams as described by Briscart & Plaizier-Vercammen (Proc. 2nd World Meeting on Pharmaceutics, Biopharmaceutics and Pharmaceutical Technology, APGI/APV, 1998, 1231-1232).

It is additionally known to protect transdermal therapeutic systems provided with photosensitive active ingredients by means of visually noticeable aluminized or lacquered cover sheets as backing layer of the TTS. DE-A1-19912623 describes a method for protecting therapeutic preparations, systems or ingredients thereof, the intention being to achieve protection, specific in each case, against breakdown by harmful factors such as atmospheric oxygen, water and/or light. Photoprotective substances which absorb or reflect electromagnetic waves are used, employing absorbing or reflecting agents whose absorption or reflection spectrum covers the wavelength range responsible for the instability of the photosensitive material or its ingredients. Coloured plastic sheets are used inter alia as cover sheet in this case, shown by the example of the 1,4-dihydropyridine derivative lacidipine.

The colouring of highly flexible plastic sheets proves to be difficult and does not provide reliable protection from light owing to fissures which frequently occur in the coloured layer of the plastic sheet.

Furthermore, DE-C1-10053375 discloses transdermal therapeutic systems (TTS) which consist of an active ingredient-containing polymer matrix and a backing layer, with polymer matrix and backing layer being firmly connected and forming a laminate, and both the polymer matrix and the backing layer containing a colourless substance which absorbs in the UV region and which has no intrinsic pharmacological effect. This solution is disadvantageous in that interaction of the colourless substance which absorbs in the UV region with the active ingredient in the polymer matrix in some cases results in an unwanted influence on the stability of the TTS, in that the firm connection between polymer matrix and backing layer which is permeable to active ingredient may result in extensive unacceptable diffusion of active ingredient from the polymer matrix into the backing layer, principally in the case of backing layers composed of polypropylene, polyethylene or polyurethane, and may finally emerge or crystallize out on the upper side of the backing layer/cover sheet, in that skin irritation may be caused through direct contact of the skin with the substances which absorb in the UV region and which are present in the backing layer/cover sheet.

It is therefore an object of the invention to provide a pharmaceutical preparation which is provided with a photosensitive active ingredient and is to be administered transdermally, and which achieves high stability without the aforementioned disadvantages.

The object is achieved according to the invention by a transdermal therapeutic system (TTS) consisting of a backing layer, of at least one active ingredient-containing matrix and optionally of a detachable sheet, and comprising a UV absorber, with at least one UV absorber-containing adhesive layer being provided between the backing layer and the active ingredient-containing matrix which is furthest away from the surface of the skin, and at least one separating layer which is impermeable to active ingredient and impermeable to the UV absorber being present between the adhesive layer containing the UV absorber and the active ingredient-containing matrix which is furthest away from the surface of the skin.

The sequence of layers in the transdermal therapeutic system starting from the side facing away from the skin can according to the invention be backing layer, UV absorber-containing adhesive layer, separating layer and finally a mono- or bilayer active ingredient-containing matrix whose pressure-sensitive adhesive surface is covered by a detachable protective sheet. The separating layer in the transdermal therapeutic system may moreover have according to the invention a layer thickness of from 4 to 23 µm, preferably from 4 to 10 µm, and consist of a barrier polymer. Suitable barrier polymers are polyethylene terephthalate, polyacrylonitrile, polyvinyl chloride, polyvinylidene chloride or its copolymers or colaminates. The matrix in the transdermal therapeutic system of the invention may be designed to be self-adhesive and have no membrane controlling the release of active ingredient, and consist essentially of polymers selected from the group of polyisobutylene, polybutene, polyacrylate, polydimethylsiloxane, styrene/isoprene block polymer or polyisoprene. The weight per unit area of the matrix can be according to the invention from 30 to 150 g/m$^2$, preferably 50 to 120 g/m$^2$, particularly preferably about 100 g/m$^2$.

The backing layer in the transdermal therapeutic system of the invention may be a transparent sheet from the group of polypropylene, polyethylene, polyurethane, polyester, ethylene/vinyl acetate copolymer or polyethylene terephthalate or mixtures thereof and may be permeable to active ingredient.

The UV absorber in the transdermal therapeutic system of the invention may moreover be present in dissolved form in the adhesive layer in a concentration of from 0.5 to 10% (m/m), preferably 1.0 to 5.0% (m/m), particularly preferably 2.0 to 4.0% (m/m), and the adhesive layer may be designed to be self-adhesive and consist essentially of polymers selected from the group of polyisobutylene, polybutene, polyacrylate, polydimethylsiloxane, styrene/isoprene block polymer or polyisoprene. The adhesive layer may moreover have a weight per unit area of from 5 to 50 g/m$^2$, preferably 20 to 30 g/m$^2$.

The adhesive layer in the transdermal therapeutic system of the invention may also have exclusively the UV absorber(s), it being possible for the latter to be colourless or yellowish.

The adhesive layer in the transdermal therapeutic system of the invention may moreover have a UV absorber content composed of a mixture of two or more substances which absorb in the UV region, it being possible to select the UV absorber(s) from the group of p-amino-benzoic acid, aminobenzoic acid derivative, preferably 2-ethylhexyl 4-dimethylaminobenzoate and/or polyethoxy-ethyl 4-bis(polyethoxyl)aminobenzoate, cinnamic acid, cinnamic acid derivatives, preferably isoamyl 4-methoxycinnamate and/or 2-ethylhexyl 4-methoxycinnamate, 3-benzylidenebornan-2-one, benzylidenebornan-2-one derivatives, preferably 3-(4')-methylbenzylindenebornan-2-one, 3-(4-sulphone)-benzylidenebornan-2-one and/or 3-(4'-trimethyl-ammonium) benzylidenebornan-2-one methylsulphate, salicylic acid derivative, preferably 4-isopropylbenzyl salicylate, 2-ethylhexyl salicylate, and/or 3,3,5-trimethylcyclohexyl salicylate, benzotriazoles, preferably 2-(5-chloro-2H-benzotriazole-2-yl)-6-(1,1-dimethylethyl)-4-methylphenol, 2,4,6'-trianiline-p-(carbo-2'-ethylhexyl-1'-oxy)-1,3,5-triazine, 3-imidazol-4-ylacrylic acid, 3-imidazol-4-yl-3-imidazol-4-ylacrylic ester, 2-phenylenebenzimidazole-5-sulphonic acid and/or its K, Na and triethanolamine (=TEA) salts, 2-cyano-3,3-diphenylacrylic acid, terephthaloylidenedicamphorsulphonic acid, butyl-methoxydibenzoylmethane, benzophenone and/or benzophenone derivatives, preferably benzophenone-3 and/or benzophenone-4. The UV absorber(s) may moreover be colourless or yellowish.

A further possibility is for the transdermal therapeutic system of the invention to be transparent or slightly opaque.

The active pharmaceutical ingredient acting in the transdermal therapeutic system of the invention may be at least one hormone and be progestogen(s), preferably gestodene or levonorgestrel.

The transdermal therapeutic system of the invention has the following advantages over conventional systems with photosensitive active ingredient content:

It is possible by varying the thickness of the layer containing the UV absorber or the concentration of the UV absorber therein to adjust accurately the desired UV protection. This is a considerable advantage over the use of conventional TTS with incorporated UV protection.

Contact between the UV absorber and the active ingredient or active ingredients in the active ingredient-containing matrix is precluded, so that neither the UV absorber nor its breakdown products which may arise under the influence of light can react with the active ingredient(s).

If a cover sheet which is permeable to active ingredient is used, diffusion of active ingredient on storage of the system may reach unacceptably high levels, so that active ingredient may emerge or crystallize out on the surface of the cover sheet. This effect can be observed for example with cover sheets composed of polypropylene, polyethylene or polyurethane. The separating layer provided according to the invention between the layer with UV absorber and the active ingredient-containing layer now represents a barrier against loss of active ingredient by diffusion through the cover sheet.

In addition, contact of the skin with UV absorbers, and thus possible skin irritation, can be avoided.

The invention and its advantageous properties are explained in detail by the following examples.

EXAMPLE 1

Two formulations of a photosensitive active ingredient from the group of progestogens were produced.

Formulation I contains an adhesive layer and a separating layer, with the adhesive layer containing 3% by weight of a UV-absorbing substance.

Formulation II contains no adhesive layer and separating layer and serves as comparative formulation. Both formulations contain an active ingredient-containing matrix with a photosensitive progestogen and were provided with a polyethylene backing layer, resulting in a TTS in each case.

Formulation I has the following composition:
1. Active ingredient-containing matrix:
1.9% progestogen
98.1% polyisobutylene-based adhesive
2. Adhesive layer:
3% Tinuvin® 326
97% polyisobutylene-based adhesive Tinuvin®326 (from CIBA, Lampertheim) is a UV absorber of the hydroxyphenylbenzotriazole class.

To investigate the light protection effect, both formulations were irradiated with light having a UV spectrum of 300-800 nm over a period of up to 14 h. The radiation source used was a xenon lamp. A filter system (type: Suprax® filter) was placed between the radiation source and the samples to be irradiated in order to simulate the irradiation under realistic conditions of TTS use. The active ingredient content in the TTS was then determined. It emerged that the TTS of formulation A containing an adhesive layer with UV-absorbing substance and a separating layer still contained about 99% of the originally employed amount of the photosensitive active ingredient after irradiation for 14 h, whereas the TTS of formulation B contained only about 24% of the originally employed amount of the photosensitive active ingredient after irradiation for only 7 h. This shows that the system of the invention displays improved protection from the sun under realistic conditions of use, because the UV-protective effect of the system of the invention (formulation A) was considerably greater than that of the comparative system (formulation B).

EXAMPLE 2

Formulation with a photosensitive active ingredient from the group of progestogens with, in each case, an adhesive layer and separating layer, in which the separating layers consists of polyethylene terephthalate (Hostaphan® from Mitsubishi Polyester, Wiesbaden).

The formulation has the following composition:
1. Active ingredient-containing matrix:
1.9% progestogen
98.1% polyisobutylene-based adhesive
2. Adhesive layer 1 and 2:
3% Uvinul®MC80
97% polyacrylate-based adhesive Uvinul®MC 80 (from BASF, Ludwigshafen) is a methoxy-cinnamic acid derivative.

EXAMPLE 3

Formulation with a photosensitive active ingredient from the group of progestogens with, in each case, two adhesive layers and separating layers, in which the separating layers consist of polyethylene terephthalate (Hostaphan® from Mitsubishi Polyester, Wiesbaden).

Formulation I has the following composition:
3. Active ingredient-containing matrix:
1.9% progestogen
98.1% polyisobutylene-based adhesive
4. Adhesive layer 1 and 2:
3% Uvinul®M40
97% polyacrylate-based adhesive Uvinul®M40 (from BASF, Ludwigshafen) is a benzophenone derivative.

EXAMPLE 4 to 12

Formulation with a photosensitive active ingredient from the group of progestogens with, in each case, at least one adhesive layer and separating layer, in which the active ingredient-containing matrix is configured in analogy to Examples 1 to 3, and the adhesive layer comprises a polyisobutylene-based adhesive and has the following compositions.

| Composition of the adhesive layer | Example 4 | Example 5 | Example 6 | Example 7 | Example 8 | Example 9 | Example 10 | Example 11 | Example 12 |
|---|---|---|---|---|---|---|---|---|---|
| Tinuvin ® 326 [%] | 2 | 2 | 2 | 3 | 3 | 3 | 4 | 4 | 4 |
| Polyiso-butylene-based adhesive [%] | 98 | 98 | 98 | 97 | 97 | 97 | 96 | 96 | 96 |
| Weight per unit area [g/m$^2$] | 20 | 30 | 50 | 20 | 30 | 50 | 20 | 30 | 50 |

EXAMPLE 13 to 21

Formulation with a photosensitive active ingredient from the group of progestogens with, in each case, at least one adhesive layer and separating layer, in which the active ingredient-containing matrix is configured in analogy to Examples 1 to 3, and the adhesive layer comprises a polyacrylate-based adhesive and has the following compositions.

| Composition of the adhesive layer | Example 13 | Example 14 | Example 15 | Example 16 | Example 17 | Example 18 | Example 19 | Example 20 | Example 21 |
|---|---|---|---|---|---|---|---|---|---|
| Tinuvin ® 326 [%] | 2 | 2 | 2 | 3 | 3 | 3 | 4 | 4 | 4 |
| Polyacrylate-based adhesive [%] | 98 | 98 | 98 | 97 | 97 | 97 | 96 | 96 | 96 |
| Weight per unit area [g/m$^2$] | 20 | 30 | 50 | 20 | 30 | 50 | 20 | 30 | 50 |

EXAMPLE 22 to 30

Formulation with a photosensitive active ingredient from the group of progestogens with, in each case, at least one adhesive layer and separating layer, in which the active ingredient-containing matrix is configured in analogy to Examples 1 to 3, and the adhesive layer has the following compositions.

| Composition of the adhesive layer | Example 22 | Example 23 | Example 24 | Example 25 | Example 26 | Example 27 | Example 28 | Example 29 | Example 30 |
|---|---|---|---|---|---|---|---|---|---|
| Uvinul ® MC80 | 2 | 5 | 8 | — | — | — | — | — | — |
| Uvinul ® M40 | — | — | — | 2 | 5 | 8 | 2 | 5 | 8 |
| Polyiso-butylene-based adhesive [%] | 98 | 95 | 92 | 98 | 95 | 92 | — | — | — |
| Polyacrylate-based adhesive [%] | — | — | — | — | — | — | 98 | 95 | 92 |
| Weight per unit area [g/m$^2$] | 20 | 30 | 50 | 20 | 30 | 50 | 20 | 30 | 50 |

The invention claimed is:

1. A transdermal therapeutic system (TTS) consisting of: a backing layer, at least one UV-absorber containing self-adhesive layer, at least one separating layer, at least one active ingredient-containing matrix layer, and optionally a detachable sheet, wherein:

i) the at least one UV absorber-containing self-adhesive layer is provided between the backing layer and the active ingredient-containing matrix layer which is furthest away from the surface of the skin, ii) the at least one active ingredient-containing matrix layer contains at least one active ingredient which is a photosensitive active ingredient, iii) the at least one separating layer has a layer thickness of from 4 to 23 μm, is impermeable to the active ingredient and impermeable to the UV absorber, and at least one separating layer is present between the UV absorber-containing self-adhesive layer and the active ingredient-containing matrix layer which is furthest away from the surface of the skin.

2. A transdermal therapeutic system according to claim 1, wherein the sequence of layers in the system starting from the side facing away from the skin is backing layer, UV absorber-containing self-adhesive layer, separating layer, and a mono- or bilayer active ingredient-containing matrix layer having a pressure-sensitive adhesive surface which is covered by a detachable protective sheet.

3. A transdermal therapeutic system according claim 1, wherein the weight per unit area of the UV absorber-containing self-adhesive layer is from 5 to 50 g/m$^2$.

4. A transdermal therapeutic system according to claim 1, wherein the separating layer consists of a barrier polymer comprising polyethylene terephthalate, poly-acrylonitrile, polyvinyl chloride, polyvinylidene chloride or copolymers or colaminates thereof.

5. A transdermal therapeutic system according to claim 1, wherein the active ingredient-containing matrix layer is self-adhesive and comprises a polyisobutylene, polybutene, polyacrylate, polydimethylsiloxane, styrene/isoprene block polymer or polyisoprene polymer.

6. A transdermal therapeutic system according claim 1, wherein the weight per unit area of the active ingredient-containing matrix layer(s) is from 30 to 150 g/m$^2$.

7. A transdermal therapeutic system according to claim 1, wherein the backing layer is permeable to the active ingredient and comprises polypropylene, polyethylene, polyurethane, ethylene/vinyl acetate copolymer or a multilayer composite of these materials with one another or with other materials.

8. A transdermal therapeutic system according to claim 1, wherein the UV absorber is present in dissolved form in the UV absorber-containing self-adhesive layer in a concentration of from 0.5 to 10% (m/m).

9. A transdermal therapeutic system according to claim 1, wherein the UV absorber(s) are contained only in the UV absorber-containing self-adhesive layer.

10. A transdermal therapeutic system according to claim 1, wherein at least one UV absorber is selected from the group consisting of: p-aminobenzoic acid, 2-ethylhexyl 4-dimethylaminobenzoate, polyethoxyethyl 4-bis(polyethoxyl)aminobenzoate, cinnamic acid, isoamyl 4-methoxycinnamate, 2-ethylhexyl 4-methoxycinnamate, 3-benzylidenebornan-2-one, 3-(4')-methylbenzylindenebornan-2-one, 3-(4-sulphone)benzylindenebornan-2-one, 3-(4'-trimethylammonium)-benzylidenebornan-2-one methylsulphate, 4-isopropylbenzyl salicylate, 2-ethylhexyl salicylate, 3,3,5-trimethylcyclohexyl salicylate, 2-(5-chloro-2H-benzotriazole-2-yl)-6-(1,1-dimethylethyl)-4-methylphenol, 2,4,6'-trianiline-p-(carbo-2'-ethylhexyl-1'-oxy)-1,3,5-triazine, 3-imidazol-4-ylacrylic acid, 3-imidazol-4-yl-3-imidazol-4-ylacrylic ester, 2-phenylenebenzimidazole-5-sulphonic acid or its K, Na, or triethanolamine salts, 2-cyano-3,3-diphenylacrylic acid, terephthaloylidenecamphorsulphonic acid, butylmethoxydibenzoylmethane, benzophenone, benzophenone-3, and benzophenone-4.

11. A transdermal therapeutic system according to claim 1, wherein the UV absorber(s) is/are colourless or yellow.

12. A transdermal therapeutic system according to claim 1, wherein the system is transparent.

13. A transdermal therapeutic system according to claim 1, wherein the active ingredient comprises at least one hormone.

14. A transdermal therapeutic system according to claim 1, wherein the active ingredient comprises a progestogen.

15. A transdermal therapeutic system according to claim 1, wherein the active ingredient comprises gestodene or levonorgestrel.

16. A transdermal therapeutic system according to claim 1, wherein the active ingredient comprises gestodene.

17. A transdermal therapeutic system according to claim 1, wherein said separating layer comprises a polyethylene terephthalate barrier polymer.

18. A transdermal therapeutic system according to claim 1, wherein said backing layer comprises a polyethylene.

19. A transdermal therapeutic system according to claim 1, wherein at least one active ingredient-containing matrix and/or at least one UV absorber-containing self-adhesive layer comprise a polymer selected from the group consisting of polyisobutylene, polybutene, polyacrylate, polydimethylsiloxane, styrene/isoprene block polymer, polyisoprene and combinations thereof.

20. A transdermal therapeutic system according to claim 1, wherein the weight per unit area of the UV absorber-containing self-adhesive layer is from 20 to 30 g/m$^2$.

21. A transdermal therapeutic system according to claim 1, wherein the separating layer has a layer thickness of from 4 to 10 μm.

22. A transdermal therapeutic system according to claim 1, wherein the weight per unit area of the active ingredient-containing matrix layer is from 50 to 120 g/m$^2$.

23. A transdermal therapeutic system according to claim 1, wherein the UV absorber is present in dissolved form in the UV absorber-containing self-adhesive layer in a concentration of from 1.0 to 5.0% (m/m).

* * * * *